Figure 1:
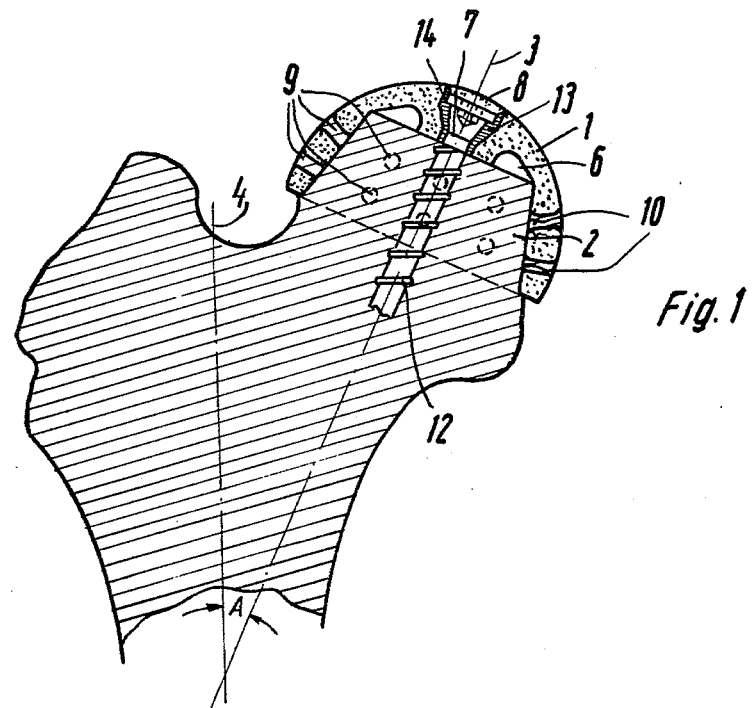

United States Patent [19]

Weber

[11] 4,224,699
[45] Sep. 30, 1980

[54] CAP-SHAPED ENDOPROSTHESIS FOR A FEMORAL HEAD

[75] Inventor: Bernhard G. Weber, St. Gall, Switzerland

[73] Assignee: Sulzer Brothers Limited, Winterthur, Switzerland

[21] Appl. No.: 908,699

[22] Filed: May 23, 1978

[30] Foreign Application Priority Data

May 23, 1977 [CH] Switzerland .................. 6309/77

[51] Int. Cl.³ .................................. A61F 1/03
[52] U.S. Cl. ......................... 3/1.913; 128/92 CA
[58] Field of Search ............. 3/1.913, 1.912, 1.9, 3/1.91, 1.911; 128/92 CA

[56] References Cited

U.S. PATENT DOCUMENTS

| | | | |
|---|---|---|---|
| 2,668,531 | 2/1954 | Haboush | 3/1.912 |
| 3,053,251 | 9/1962 | Black et al. | 128/92 CA |
| 3,140,712 | 7/1964 | Hunter | 3/1.91 X |
| 3,521,302 | 7/1970 | Müller | 3/1.91 |
| 3,596,656 | 8/1971 | Kaute | 128/92 D |
| 3,894,297 | 7/1975 | Mittelmeier et al. | 3/1.912 |
| 3,938,198 | 2/1976 | Kahn et al. | 3/1.912 |
| 4,077,070 | 3/1978 | Sivash | 3/1.912 |

FOREIGN PATENT DOCUMENTS 471394  5/1952  Italy .................. 128/92 CA

*Primary Examiner*—Clifford D. Crowder
*Attorney, Agent, or Firm*—Kenyon & Kenyon

[57] ABSTRACT

The cap-shaped endoprosthesis is formed of a cap-shaped shell and an anchoring pin which extends through a bore in the shell. In addition, the peripheral edge of the shell is provided with a plurality of apertures into which tissue may invade to aid in securing the shell to the femoral head. Where the shell and pin are made of different materials, a plastic member maintains the pin and shell out of contact with each other.

5 Claims, 2 Drawing Figures

U.S. Patent

Sep. 30, 1980

4,224,699

CAP-SHAPED ENDOPROSTHESIS FOR A FEMORAL HEAD

Heretofore, if for traumatic or pathological reasons it is necessary to replace substantially only the spherical surface of a femoral head, a prosthesis of cap-shaped construction is generally used. However, difficulties often occur in securing such cap-shaped prosthesis to an operatively prepared bone.

One known cap-shaped endoprosthesis, for example, as described in German Offenlegungschrift No. 2,535,649, includes a cap-shaped shell, a pressure plate and an anchor pin which extends through the pressure plate from the rear into the shell. The pin is exposed to bear externally on the bone below the greater trochanter with forces transmitted to the bone through the pressure plate. In this construction, however, the shell of the prosthesis is anchored in a very eccentric manner and is disposed near the main blood vessels for supplying the bone. Because the eccentric mounting increases the tilting moment, there is a risk that the shell may work loose over a period of time.

As is known, shells of the type used in the endoprosthesis are frequently made of a bioceramic material or of a pyrolytic carbon whereas anchoring pins are generally made of metal or metal alloys. However, if these materials make direct contact with one another and slide or rub together even very slightly, there is a considerable amount of abrasion which takes place. Such abrasion is usually unacceptable.

Accordingly, it is an object of the invention to improve the long-term anchorage of cap-shaped prostheses.

It is another object of the invention to permit anchoring of a cap-shaped prosthesis for a femoral head away from the main blood vessels of the femoral bone.

It is another object of the invention to provide a cap-shaped endoprosthesis of relatively simple construction.

It is another object of the invention to obviate abrasion between components of cap-shaped prosthesis which are made of different materials.

Briefly, the invention provides a cap-shaped endoprosthesis for a femoral head which is comprised of a cap-shaped shell and an anchoring pin. The shell is constructed to define a cavity for fitting over a femoral head and includes a bore which extends through the shell and a plurality of apertures which are distributed about a peripheral edge of the shell. The anchoring pin extends through the bore in order to anchor the shell to the femoral head while the apertures allow an invasion of tissue so as to further secure the shell in place.

By positioning the bore for the anchoring pin in a shell surface, there is a considerable reduction in the tilting moments of the shell. These moments are particularly very small when the bore is disposed centrally on the shell. Further, there are far fewer limitations on the location of the bore for the anchoring pin. Consequently, the bore can be positioned so as to obviate the risk of damage to the main blood vessels supplying the bone.

Since tissue can invade the shell via the peripheral apertures, there is a resulting improvement in long term fixing. In order to promote the invasion of this tissue and to obviate stress peaks, the apertures can widen in trumpet fashion at least inwardly towards the shell cavity from a central cross-section of shell thickness. That is, the apertures widen from a midlength of the aperture.

In order to prevent accidental turning of the shell on the bone, the shell cavity is made with a regular polygonal shape in at least one circumferential portion and the bone is shaped in corresponding manner during implantation.

In order to obviate any abrasion between the shell and the anchoring pin where the shell and pin are made of disparate materials, a plastic member is disposed between the pin and shell to maintain the pin and shell out of contact with each other. Further, in order to avoid any creep in the plastic member, the pin and shell are shaped to define a gap with narrowing sections at exposed boundaries i.e. ends of the gap while the plastic member fills the gap and has thin-walled extensions in the narrowing sections of the gap.

Figure 2:
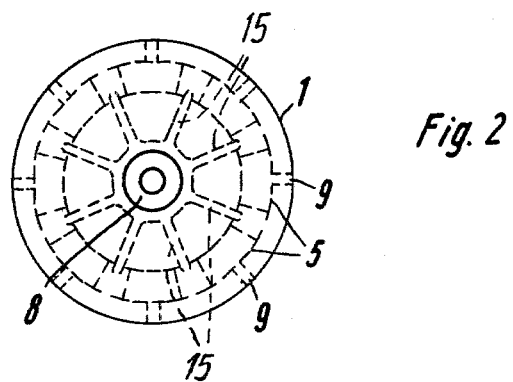

These and other objects and advantages of the invention will become more apparent from the following detailed description taken in conjunction with the accompanying drawings wherein:

FIG. 1 illustrates a longitudinal sectional view taken on line I—I of FIG. 2 through an endoprosthesis secured to a femoral head in accordance with the invention; and FIG. 2 illustrates a back view of the prosthesis.

Referring to FIG. 1, the endoprosthesis is constructed with a cap-shaped hemispherical shell 1 which is made of a known bio-ceramic material or pyrolytic carbon and has a cavity 6 which fits over a femoral head 2. The femoral head 2 is treated so that the central axis 3 of the shell 1 forms an angle A with the axis 4 of the femur. In addition, the shell cavity has a regular polygonal shape 5 in a bottom circumferential portion of the cavity 6 while the prosthesis receiving stump of the femoral head 2 has a corresponding polygonal peripheral shape. The mating polygonal shapes between the head 2 and the shell 1 reduce or completely obviate the risk of accidental rotation of the prosthesis, once fitted on the femoral stump.

As shown in FIG. 1, the shell 1 has a bore 8 which extends therethrough on the central axis 3 and which receives a fixing or anchoring pin 7. In addition, the shell 1 is provided with a plurality of apertures 9 which are distributed about the peripheral edge of the shell 1. These apertures 9 are adapted for the invasion of tissue and have their narrowest cross-section in the middle thickness of the shell 1. As shown, each aperture 9 widens in the shape of a trumpet-like funnel 10 at least inwardly towards the cavity 6 from a central cross-section of shell thickness. Each aperture 9 may also widen in the same fasion outwardly. The inwardly extending widening particularly boosts the invasion of tissue without high stress peaks.

As shown in FIG. 2, the shell 1 has a plurality of radial ribs 15 within the cavity 6. These ribs 15 function to reinforce the shell 1. Further, tissue may grow into the area between the ribs 15 in the course of time as indicated in FIG. 1.

The anchoring pin 7 is made of metal or a metal alloy and extends through the bore 8 on the central axis 3 to retain the shell 1 on the femoral head 2 and is, for example, screwed into the boney substance of the femoral bone through the agency of a screw thread 12.

In order to preclude any direct contact between the material of the metal pin 7 and the material of the bioceramic shell 1, a plastic member 13 in the form of an insert or liner is placed between the pin 7 and the shell 1. To this end, the pin 7 and the shell 1 are sized to define a shaped gap therebetween with narrowing sections at exposed boundries i.e. at the ends of the gap. In addition, the plastic member 13 which can be made of ultra-high molecular weight polyethylene fills the gap and has thin-walled extensions 14 which extend into the narrowing sections. This insures that the plastic member 13 cannot creep over a long term.

The invention thus provides a cap-shaped endoprosthesis which can be easily mounted on a prepared femoral bone and secured in place without the need for adhesives. Further, the mounting of the implant is such as to reduce tilting moments considerably.

What is claimed is:

1. A cap-shaped endoprosthesis for a femoral head, said endoprosthesis comprising:
   a cap-shaped hemispherical shell of bioceramic material defining a cavity for fitting over a femoral head, said shell having a bore extending centrally therethrough and a plurality of apertures distributed about a peripheral edge thereof for an invasion of tissue therein;
   a metal anchoring pin extending through said bore for anchoring said shell to a femoral head, said pin and said shell defining a shaped gap therebetween with narrowing sections at each end of said gap; and
   a plastic member disposed between said pin and said shell to maintain said pin and said shell out of contact with each other, said plastic member filling said gap and having thin-walled extensions in said narrowing sections.

2. A cap-shaped endoprosthesis as set forth in claim 1 wherein each aperture widens in trumpet-fashion at least inwardly towards said cavity from a central cross-section of shell thickness.

3. a cap-shaped endoprosthesis as set forth in claim 1 wherein said cavity is of regular polygonal shape in at least one circumferential portion thereof.

4. A cap-shaped endoprosthesis for a femoral head, said endoprosthesis comprising
   a cap-shaped shell of bioceramic material or pyrolytic carbon defining a cavity of regular polygonal shape in at least one circumferential portion thereof for fitting over a correspondingly shaped femoral head, said shell having a bore extending centrally therethrough and a plurality of apertures distributed about a peripheral edge thereof for an invasion of tissue therein, each said aperture widening in trumpet-fashion at least inwardly towards said cavity from a central cross-section of shell thickness; and
   a metal anchoring pin extending through said bore and having a screw thread for anchoring said shell to a femoral head.

5. A cap-shaped endoprosthesis as set forth in claim 4, which further comprises a plastic member between said pin and said shell to maintain said pin out of contact with said shell.

* * * * *